(12) United States Patent
Randzio et al.

(10) Patent No.: US 6,750,062 B1
(45) Date of Patent: Jun. 15, 2004

(54) METHOD AND DEVICE FOR STUDYING THE EFFECT OF A SUPERCRITICAL FLUID ON THE TRANSITION OF A MATERIAL FROM ONE CONDENSED PHASE TO THE OTHER AND THEIR APPLICATION IN THE CASE OF A POLYMER MATERIAL

(75) Inventors: Stanislaw L. Randzio, Varsovie (PL); Jean-Pierre E. Grolier, Clermont-Ferrand (PL)

(73) Assignee: Centre National de la Recherche Scientifique (CNRS), Paris (FR)

(*) Notice: Subject to any disclaimer, the term of this patent is extended or adjusted under 35 U.S.C. 154(b) by 0 days.

(21) Appl. No.: 09/555,805
(22) PCT Filed: Dec. 3, 1998
(86) PCT No.: PCT/FR98/02612
§ 371 (c)(1),
(2), (4) Date: Jul. 14, 2000
(87) PCT Pub. No.: WO99/28731
PCT Pub. Date: Jun. 10, 1999

(30) Foreign Application Priority Data

Dec. 3, 1997 (FR) .............................. 97 15221

(51) Int. Cl.$^7$ .............................. G01N 25/20
(52) U.S. Cl. ............. 436/147; 436/148; 436/174; 436/55; 422/51; 422/82.12; 422/82.13
(58) Field of Search ............... 436/147, 148, 436/55, 174; 422/51, 82.12, 82.13

(56) References Cited

U.S. PATENT DOCUMENTS 4,500,432 A * 2/1985 Poole et al. ............... 210/659

FOREIGN PATENT DOCUMENTS

| DE | 116 504 | 11/1975 |
|----|---------|---------|
| EP | 0 357 176 | 3/1990 |
| EP | 0 610 953 | 8/1994 |
| FR | 2 679 650 | 1/1993 |

OTHER PUBLICATIONS

Han et al. "Processing of poly(ethylene–co–1–butene) and polypropylene from subcritical and supercritical propane solution" Polymeric Materials Science and Engineering, 1996, v. 75, pp. 279–280.*

* cited by examiner

*Primary Examiner*—Jill Warden
*Assistant Examiner*—Yelena Gakh
(74) *Attorney, Agent, or Firm*—Foley & Lardner

(57) ABSTRACT

The invention concerns the study of the effect of a supercritical fluid on the transitions of a material, which consists in varying continuously or by stages according to a predetermined programme, a first parameter value selected among the super-critical fluid pressure, the temperature of a cell containing the material sample and said sample volume, while maintaining a second of said parameters at a value selected, so as to induce the transition; and in recording the variation of the first parameter, that of the third parameter and the heat flow rate in the cell; in comparing said recordings with those obtained by replacing the supercritical fluid with a neutral fluid. The figure shows a diagram of the device for carrying out said study. The invention is in particular useful for studying a polymer material transitions.

26 Claims, 5 Drawing Sheets

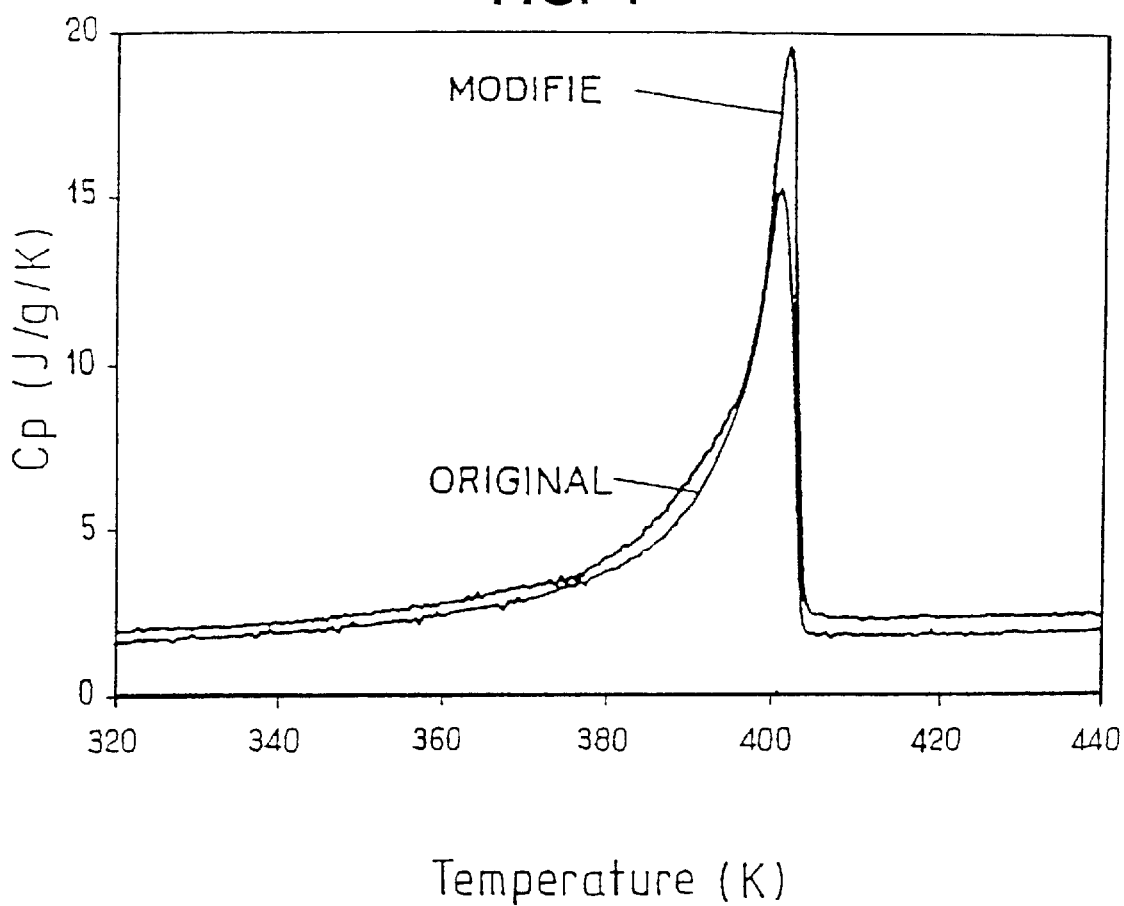

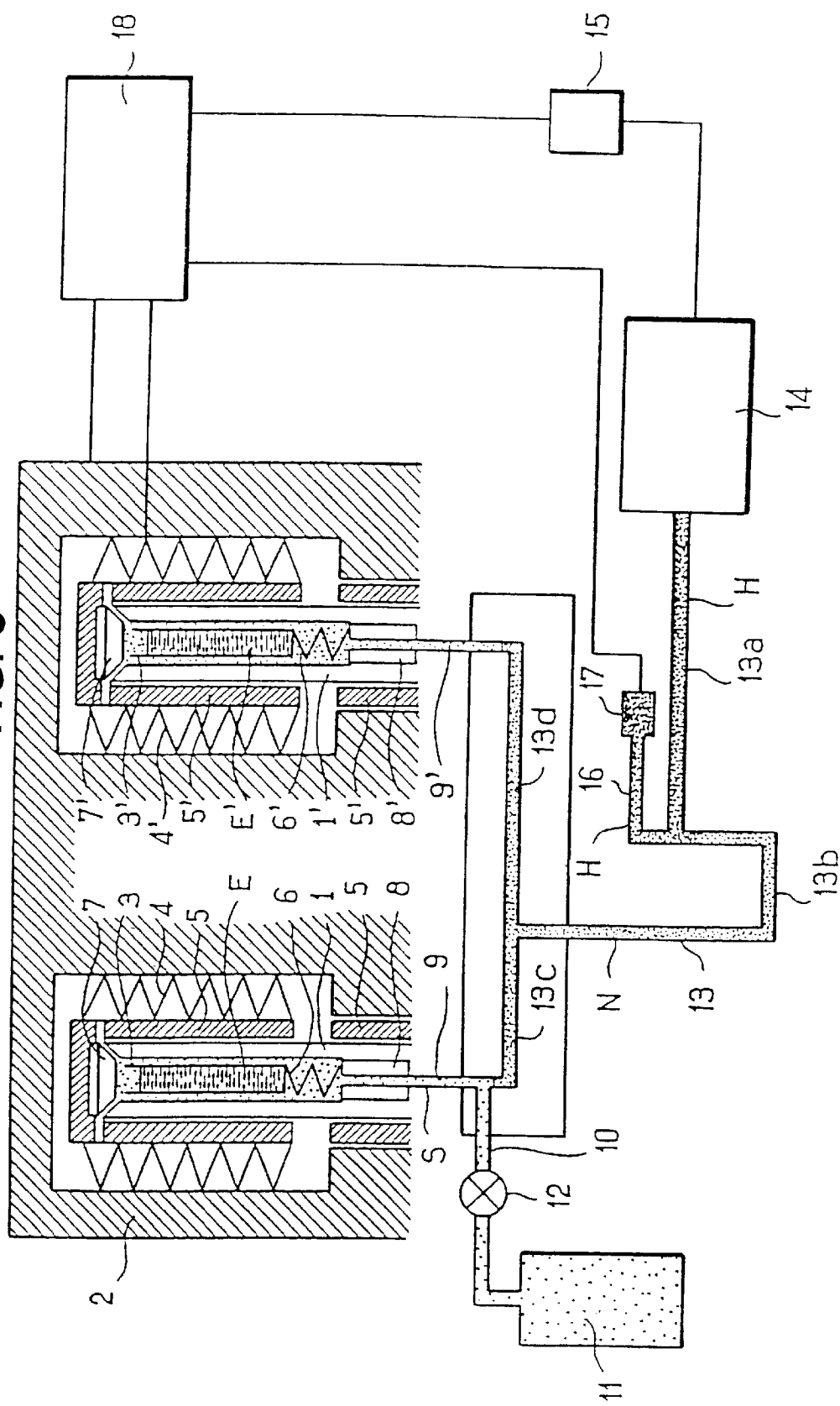

METHOD AND DEVICE FOR STUDYING THE EFFECT OF A SUPERCRITICAL FLUID ON THE TRANSITION OF A MATERIAL FROM ONE CONDENSED PHASE TO THE OTHER AND THEIR APPLICATION IN THE CASE OF A POLYMER MATERIAL

The present invention relates to a method and to an apparatus for studying the effect of a supercritical fluid on the transition of a material from one of two condensed phases to the other and to their application to the case of a polymer material.

Supercritical fluids, which are neither gases nor liquids and which may be progressively compressed from a low density to a high density, are growing in importance as solvents and reaction media, especially in the chemical industry, in the pharmaceutical industry and in the food industry.

An example in which these fluids are applied in the chemical industry is especially that of polymers, the supercritical fluids of which allow the molecular weight and the morphology to be controlled, resulting in novel modified products.

Such modifications are often carried out by compressed-gas absorption or by recrystallization from solutions prepared with various liquid solvents.

In the case of modifications with gas absorption, the semicrystalline substance becomes more plastic and, for example, its glass transition may be lowered by several tens of degrees. The main drawback of such a technique is that this property is observed in practice only when the modified substance is in the presence of compressed gases. This greatly limits the use of this technique.

In the case of modifications by recrystallization from a liquid solution, the morphology of the condensed phase may be changed, but it is very often difficult to find suitable liquid solvents. This technique is therefore limited in practice to systems for which the solubilities are well known. In addition, the modified condensed phase must be suitably dried and this is a disadvantage, especially from the energy standpoint.

Although the scientific literature also reports various experimental studies involving a supercritical fluid on particular materials under specific conditions, it is apparent, however, that hitherto no apparatus has existed which allows the effect of a supercritical fluid on the transition of any material from one of two condensed phases to the other, by controlling all the significant parameters, to be fully studied.

The subject of the present invention is a method and an apparatus making it possible in particular to study the modification of the morphology of a substance solely by melting and recrystallizing the substance or simply by making it solidify from the fluid or liquid state under the pressure (at saturation) of a supercritical fluid under well-defined isothermal or isobaric conditions.

Typically, the pressure range may go up to at least 400 MPa and the temperature range may cover at least the 220–570 K interval.

The apparatus which allows the effect of a supercritical fluid on the transition of a material from one of two condensed phases to the other to be studied, comprises, according to the invention:

a cell (1) suitable for containing a specimen of the material to be studied and for withstanding the pressures and temperatures involved in the study;

a source of supercritical fluid and a pipe connecting this source to the inside of the cell for controlled introduction of this fluid into the cell so that it is in contact with the control specimen; means for varying, continuously or in steps, according to a defined program, the value of a first parameter chosen by the pressure (P) of the supercritical fluid, the temperature (T) of the cell and the volume (V) of the specimen in the cell, whilst keeping a second of said parameters at a chosen value, so as to induce the recording transition;

means for recording the variation in the first parameter, the variation in the third parameter and the variations ($\Delta H$) in the heat flux in the cell;

means for making analog recordings under similar conditions with a neutral fluid instead of the supercritical fluid.

In preferred embodiments, the apparatus of the invention also has one or more of the following characteristics:

the cell contains an open ampule which receives the specimen;

the ampule is one with a flexible wall;

the apparatus includes a high-pressure pump whose piston is actuated by a stepper motor, means for transmitting the pressure exerted by this pump to the supercritical fluid and means for controlling the stepper motor and for recording the variations in the number of steps of the motor;

a duct connects the pressure outlet of the pump to said pipe and contains the neutral fluid so that the pressure of the pump is transmitted to the supercritical fluid via the neutral fluid;

said duct includes, at the outlet of the pump, a duct part which lies upstream of the neutral fluid contained in the duct and contains a hydraulic fluid;

said duct also terminates in another cell identical to said cell so that the neutral liquid is introduced into this cell;

the cell or each cell is placed in a calorimetric detector surrounded by a thermostat;

a control and recording unit is connected to the thermostat, to the calorimetric detector, to the stepper motor and to a pressure sensor which receives the pressure exerted by the pump.

The subject of the invention is also a method for studying the effect of a supercritical fluid on the transition of a material from one of two condensed phases to the other, in which:

a specimen of the material and the supercritical fluid are introduced into a cell so that the fluid is in contact with the specimen;

the transition is induced by varying, continuously or in steps, according to a defined program, the value of a first parameter chosen by the pressure (P) of the fluid, the temperature (T) of the cell and the volume (V) of the specimen in the cell, whilst keeping a second of said parameters at a chosen value;

the variation in the first parameter, the variation in the third parameter and the variation in the heat flux in the cell are recorded;

the above operations are repeated with the same program parameter and the same chosen value but using a neutral fluid instead of the supercritical fluid, by bringing or not bringing the neutral fluid into contact with the specimen depending on the case;

and the results obtained for the two fluids are compared in order to evaluate the effect of the supercritical fluid on the transition conditions.

In preferred embodiments, the method of the invention also has one or more of the following characteristics:

a supercritical fluid chosen from carbon dioxide, nitrogen, methane, ethane, propane, or mixtures thereof, or any other fluid capable of being brought into the supercritical state, is used;

mercury is used as the neutral fluid;

the pressure of a hydraulic fluid actuated by a piston is transmitted to the supercritical fluid;

this transmission is carried out by means of the neutral fluid;

said hydraulic fluid is used to push the neutral fluid right into the cell;

said piston is displaced by the action of a stepper motor in order to create said pressure and the number of steps of the motor needed to keep the pressure at a chosen value is counted so as to determine the variation in the volume of the specimen in the cell during the transition;

the following steps are carried out: a) introduction of the supercritical fluid into the experimental cell at the pressure needed to make a high-pressure pump work; b) compression of the supercritical fluid by the high-pressure pump to the desired pressure; c) isobaric initiation of the melting of the material by controlled increase in the temperature and simultaneous recording of the changes in the volume and in the heat flux; d) isobaric initiation of the isobaric crystallization of the material by controlled reduction in the temperature and simultaneous recording of the changes in the volume and in the heat flux;

the following steps are carried out: a) introduction of the supercritical fluid into the experimental cell containing the material at the pressure needed to make the high-pressure pump work; b) compression of the supercritical fluid by the high-pressure pump to the desired pressure; c) isothermal initiation of the melting of the substance by controlled reduction in the pressure and simultaneous recording of the changes in the volume and in the heat flux; d) isothermal initiation of the isothermal crystallization of the material by controlled increase in the pressure and simultaneous recording of the changes in the volume and in the heat flux.

said material in the fluid or liquid state is modified by reducing its temperature below the controlled pressure of the supercritical fluid.

Among the applications of the invention, mention may especially be made of the study of polymer materials, in particular for determining when the supercritical fluid/polymer solution is in an equilibrium state and when this solution becomes saturated.

In particular embodiments:

the transition of the polymer is induced by varying the temperature at constant pressure;

under the same pressure conditions, a slow heating is effected in order to obtain a homogeneous, saturated supercritical gas/polymer system followed by a slow cooling in order to make a microfoam or nanofoam phase condense, whilst recording all the parameters (P,T, $\Delta$H and $\Delta$V) of the observed transitions;

the transition of the polymer is induced by varying the pressure at constant temperature;

under the same pressure conditions, a slow heating is effected in order to obtain a homogeneous, saturated supercritical gas/polymer system followed by a slow compression in order to make a microfoam or nanofoam phase condense, whilst recording all the parameters (P,T,$\Delta$H and$\Delta$V) of the observed transitions;

the stable shape of the thermogram, which does not change during the successive transitions under the atmosphere of the supercritical gas, is the indicator of the end of formation of the novel microfoam or nanofoam phase.

The description which follows, in conjunction with the appended drawing, given by way of nonlimiting example, will make it clearly understood how the invention may be realized, the particular features which emerge both from the text and from the drawing forming, of course, part of said invention:

FIG. 4 shows the variation in the thermal capacity as a function of temperature, at ambient pressure, for a treated medium-density polyethylene specimen and for an untreated specimen; and FIG. 5 is a diagram of an alternative embodiment of the apparatus of the invention.

Figure 1:
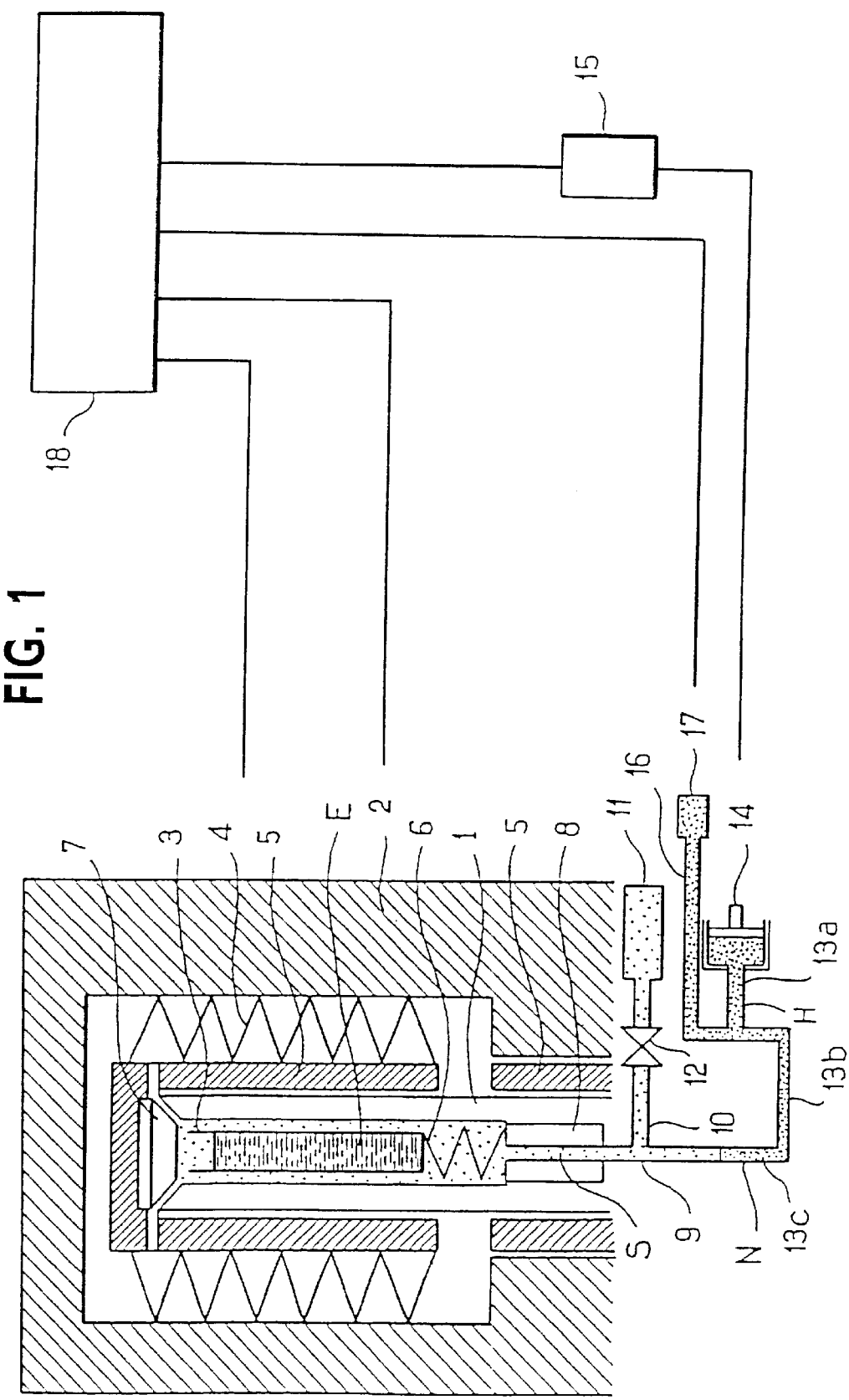
FIG. 1 shows the diagram of an apparatus for modifying and studying the properties of condensed phases.

FIG. 1 is a diagram of an apparatus according to the invention which shows a cell 1 consisting of a steel tube capable of withstanding high pressures and temperatures, which cell is placed in a thermostat 2 and contains an ampule 3 made of glass, steel or any other suitable material capable of receiving the specimen E to be studied. A calorimetric detector 4 and a heat exchanger 5 are placed between the thermostat 2 and the cell 1.

The ampule 3 is open at the top and rests in the cell on a spring 6. The cell 1 is closed at the top by a plug 7 and communicates at the bottom via a coupling 8 with a pipe 9 consisting of a steel capillary tube.

The pipe 9 is connected, firstly, via a branch 10 to a source 11 of supercritical fluid controlled by a valve 12 and, secondly, via a branch 13a, 13b, 13c located upstream of the junction between the pipes 9 and 10, to the outlet of a syringe-type pump 14 whose piston is driven by a stepper motor 15.

The supercritical fluid S contained in the pipe 9 receives the pressure of the pump 14 via a neutral fluid N contained in the pipe 13b, 13c and via a hydraulic fluid H contained in the pipe 13a and actuated by the piston of the pump.

A pipe 16 transmits the pressure of the hydraulic fluid to a pressure sensor 17.

A logic controller 18, connected to the calorimetric detector 4, to the thermostat 2, to the stepper motor 15 and to the pressure sensor 17, manages the operation of the apparatus as a function of the program set by the operator and delivers the required recorded information.

This controller controls the pressure and the temperature of the thermostat, it records the heat flux through the calorimetric detector 4 and it records the volume changes by counting the number of steps of the motor 15.

This apparatus makes it possible to vary any one of the three parameters P, V, T, in steps or continuously, one of the two other parameters being kept constant, the changes in heat flux due to the variation in the variable parameter and the variation in the third parameter, not kept constant, being recorded.

When it is desired to take measurements with the neutral fluid, the influx of the supercritical fluid is interrupted and the neutral liquid is introduced right into the cell in order to expel the supercritical fluid remaining and to replace it with the neutral fluid.

EXAMPLE

A specimen of medium-density polyethylene (MDPE, density 938 kg/m³) is introduced into the ampule.

The ampule placed in the cell is washed with supercritical methane (SCM) for a few minutes and the cell is closed. The SCM is compressed against the polymer at an initial pressure of 25–30 MPa.

The variation in the heat flux as a function of temperature is recorded at constant pressure.

Figure 2:
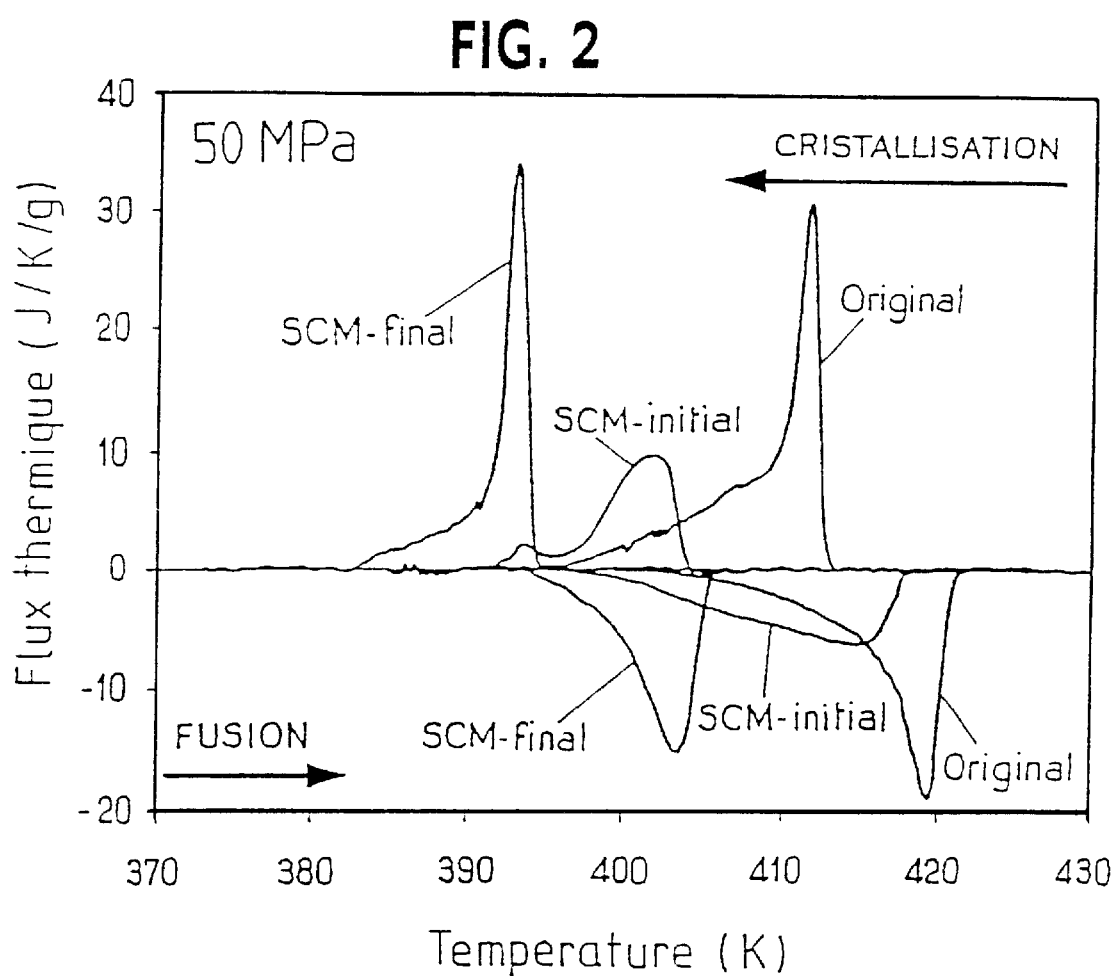
FIGS. 2 and 3 are calorimetric thermograms recorded in the case of a medium-density polyethylene treated with supercritical methane or treated with a neutral fluid, at methane pressures of 50 and 100 MPa, respectively.
Figure 3:
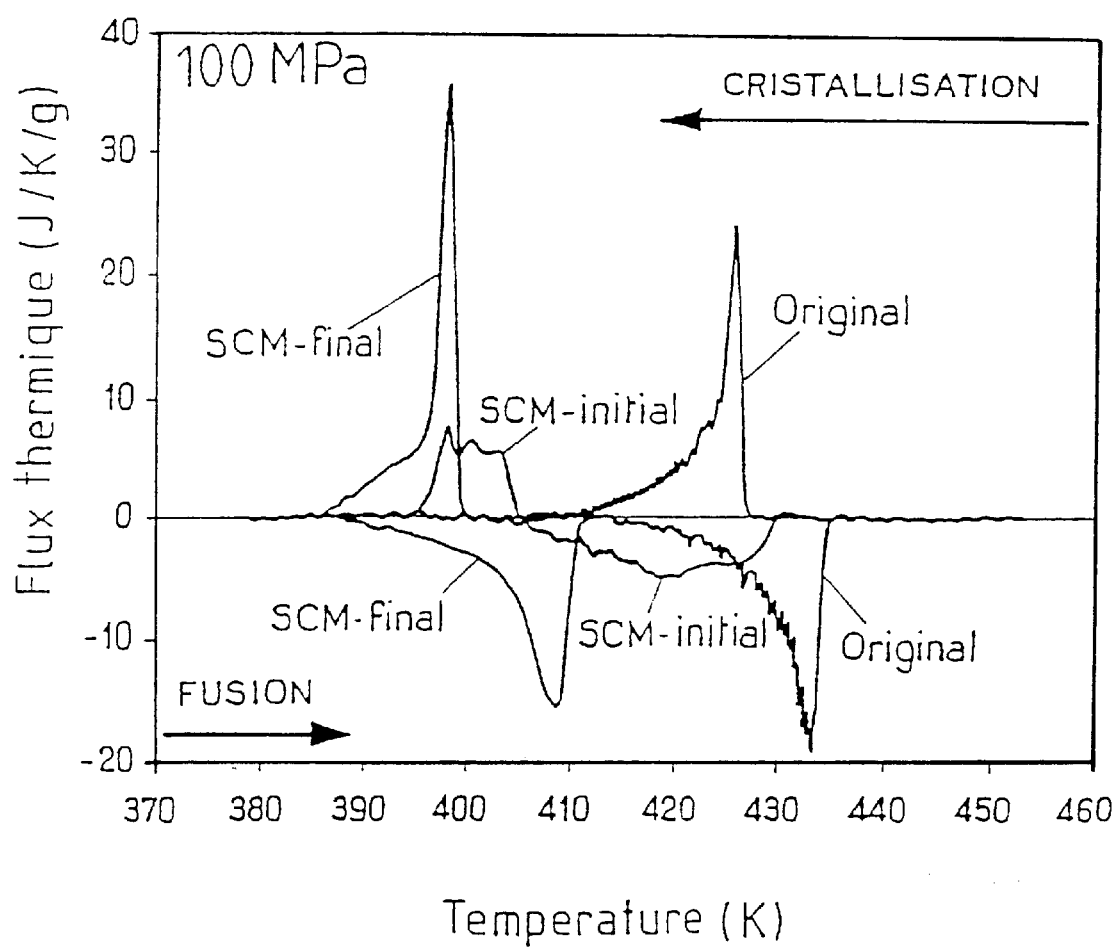

FIGS. 2 and 3 show the thermograms thus obtained, at a pressure of 50 MPa and a pressure of 100 MPa respectively, in the presence of SCM or by replacing the SCM with mercury. Since mercury does not affect the polyethylene, the corresponding thermograms are referred to as references ("original").

The "SCM-initial" curves were obtained during the first heating and cooling of a virgin specimen under compressed SCM. The "SCM-final" curves were obtained after the specimen was melted and recrystallized several times under compressed SCM.

Comparing these thermograms (shapes and magnitudes) with the original thermograms show that the interaction of the polyethylene with the supercritical fluid has an effect on the melting and on the crystallization.

The meltings and crystallizations are repeated until the thermograms no longer change. It is found that the texture of the specimen becomes similar to that of polytetrafluoroethylene, i.e. opaque and white in color. The density has dropped from 938 kg/m³ to approximately 600 kg/M³. It is found that the modified specimen is much more homogeneous than initially.

FIG. 4 shows that the thermal capacity curves of the modified MDPE have sharper transitions than those of the original MDPE.

The modified properties are stable and do not change at ambient pressure and temperature, but the modifications disappear under the effect of melting and recrystallization at atmospheric pressure.

The apparatus in FIG. 1 can be modified. FIG. 5 shows, for example, an alternative form of the apparatus in which two cells 1, 1' are provided, to receive the specimen to be studied and the supercritical fluid and to receive a specimen and the neutral fluid via a pipe 13d, respectively.

The same references, with or without a prime exponent, denote corresponding means in FIGS. 1 and 5.

The operation of the apparatus in FIG. 5 will be described below by taking as an example the modifications of the morphology of a semicrystalline polyethylene by linearly increasing and decreasing the temperature at the controlled constant pressure of the supercritical methane or by linearly decreasing and increasing the pressure of the supercritical methane at constant temperature.

A specimen of the substance to be modified, in the example of application—a medium-density polyethylene—, is introduced into the ampule of the cell 1, the cell of reference 1' this time being isolated from the hydraulic system and serving only as a known thermocontrol.

The specimen is washed in a flow of methane at room temperature in order to purge the impurities. Next, the experimental cell is closed and introduced into the calorimetric detector located in the thermostat, and the fluid is introduced and compressed to the initial pressure needed to make the high-pressure pump 15 work.

The procedure then continues according to the chosen operating mode: isobaric or isothermal.

In the case of the isobaric mode carried out with the help of the logic controller 18, the system studied is compressed by the high-pressure pump 14 to the desired pressure. After thermal and mechanical equilibrium have been established, the temperature is programmed with a very low constant rate, the pressure being kept constant, and the calorimetric thermogram and the number of steps of the motor used to compensate for the volume change during the heating are recorded. After the end of the phase change, observed especially in the calorimetric thermogram, the heating is stopped and the cooling is started at the same temperature programming rate.

The first thermograms, both for melting and for solidification, contain the thermal effects of phase changes and the effects of the interaction of the supercritical gas with the modified substance. The heating and cooling procedures are then continued until the thermograms have the stable shape. This stable shape may, moreover, be easily compared with the shape of the respective thermograms obtained for the same substance with the same procedures, but with the supercritical gas replaced with a neutral fluid, for example mercury. This replacement may be done by closing the valve 12 and by placing a virgin specimen in the cell 1; the neutral hydraulic fluid (mercury) is then taken upward to the upper end of this cell with the aid of the pump 14, after which the cell is closed with the polymer immersed in the mercury.

It is also quite possible to make this comparison in a single experiment in which the experimental cell 1 and the reference cell 1' contain the specimens of the same polymer, but the cell 1 being compressed with supercritical gas and the reference cell 1' compressed with mercury.

In the case of the isothermal mode carried out with the aid of the logic controller 18, the system studied is compressed by the high-pressure pump to the highest pressure desired and the temperature is raised to the chosen value. After thermal and mechanical equilibrium have been reached, the pressure is reduced at a very low constant rate, the temperature being kept constant, and the calorimetric thermogram and the number of steps of the motor used to compensate for the volume change during the programmed decompression are recorded. After the end of the phase change, observed especially in the calorimetric thermogram, the decompression is stopped and the compression started at the same pressure programming rate at least to the end of the isothermal solidification.

The first thermograms, both for melting and for solidification, contain the thermal effects of phase changes and the effects of the interaction of the supercritical gas with the modified substance. The decompression and compression procedures are then continued until the thermograms have the stable shape. This stable shape may, moreover, be easily compared with the shape of respective thermograms obtained for the same substance with the same procedures, but with the supercritical gas replaced with a neutral fluid, e.g. mercury; this replacement is done in the same way as in the isobaric mode described above.

Detailed analysis of the results obtained gives the thermodynamic parameters of the phase changes studied: pressures, entropies and volumes, both for the virgin substance studied under the pressure of a neutral fluid, such as mercury, and for the modified substance under the pressure of the supercritical gas. Such comparisons both under isothermal and isobaric conditions cannot be made with the methods and apparatuses known at the present time.

It goes without saying that modifications may be made to the embodiments that have just been described, especially by substituting equivalent technical means, without thereby departing from the scope of the present invention.

What is claimed is:

1. Apparatus for studying the effect of a supercritical fluid on the transition of a material from one of two condensed phases to the other, which comprises:

a cell suitable for containing a specimen of the material to be studied and for withstanding the pressures and temperatures involved in the study;

a source of supercritical fluid (S) and a pipe connecting this source to the inside of the cell for controlled introduction of this fluid into the cell so that it is in contact with the specimen;

means for varying, continuously or in steps, according to a defined program, the value of a first parameter chosen from the pressure (P) of the supercritical fluid, the temperature (T) of the cell and the volume (V) of the specimen in the cell, whilst keeping a second of said parameters at a chosen value, so as to induce the transition;

means for detecting heat flux in the cell;

means for recording the variation in the first parameter, the variation in a third of said parameters and the variations ($\Delta H$) in the heat flux in the cell;

means for making analog recordings under similar conditions with a neutral fluid instead of the supercritical fluid.

2. Apparatus according to claim 1, which comprises an ampule, optionally with a flexible wall, for containing the specimen in the cell.

3. Apparatus according to either of claims 1 and 2, which comprises a high-pressure pump whose piston is actuated by a stepper motor means for transmitting the pressure exerted by this pump to the supercritical fluid, and means for controlling the stepper motor and for recording the variations in the number of steps of the motor.

4. Apparatus according to claim 3, which comprises a duct connecting the pressure outlet of the pump to said pipe and containing the neutral fluid (N).

5. Apparatus according to claim 4, in which said duct includes a branch which terminates in another cell identical to said cell so that the neutral liquid is introduced into this other cell.

6. Apparatus according to claim 4, in which said duct includes, at the outlet of the pump, a duct part which lies upstream of the neutral fluid contained in the duct and contains a hydraulic fluid (H).

7. Apparatus according to claim 1, in which the cell or each cell is placed in a calorimetric detector surrounded by a thermostat.

8. Apparatus according to claim 4, which comprises a control and recording unit connected to the thermostat, to the calorimetric detectors, to the stepper motor and to a pressure sensor which receives the pressure exerted by the pump.

9. Method for studying the effect of a supercritical fluid on the transition of a material from one of two condensed phases to the other, in which:

a specimen of the material and the supercritical fluid are introduced into a cell so that the fluid is in contact with the specimen;

the transition is induced by varying, continuously or in steps, according to a defined program, the value of a first parameter chosen by the pressure (P) of the fluid, the temperature (T) of the cell and the volume (V) of the specimen in the cell, whilst keeping a second of said parameters at a chosen value;

the variation in the first parameter, the variation in the third parameter and the variation in the heat flux in the cell are recorded;

the above operations are repeated with the same program parameter and the same chosen value but using a neutral fluid instead of the supercritical fluid, by bringing or not bringing the neutral fluid into contact with the specimen depending on the case;

and the results obtained for the two fluids are compared in order to evaluate the effect of the supercritical fluid on the transition conditions.

10. Method according to claim 9, in which the supercritical fluid used is chosen from carbon dioxide, nitrogen, methane, ethane, propane, or mixtures thereof, and the other fluids capable of being brought to the supercritical state.

11. Method according to claim 9, in which mercury is used as the neutral fluid.

12. Method according to claim 9, further comprising transmitting pressure of a hydraulic fluid actuated by a piston to the supercritical fluid.

13. Method according to claim 12, in which the transmission is carried out by means of the neutral fluid.

14. Method according to claim 13, in which, for studying the transition of the material in the presence of the neutral fluid in the cell, said hydraulic fluid is used to push the neutral fluid night into the cell.

15. Method according to claim 12, in which said piston is displaced by the action of a stepper motor in order to create said pressure and the number of steps of the motor needed to keep the pressure at a chosen value is counted so as to determine the variation in the volume of the specimen in the cell during the transition.

16. Method according to claim 9, in which the following steps are carried out: a) introduction of the supercritical fluid into the experimental cell at the pressure needed to make a high-pressure pump work; b) compression of the supercritical fluid by the high-pressure pump to the desired pressure; c) isobaric initiation of the melting of the material by controlled increase in the temperature and simultaneous recording of the changes in the volume and in the flux and of heat; d) isobaric initiation of the isobaric crystallization of the material by controlled reduction in the temperature and simultaneous recording of the changes in the volume and in the heat flux.

17. Method according to claim 9, in which the following steps are carried out: a) introduction of the supercritical fluid into the experimental cell containing the material at the pressure needed to make the high-pressure pump work; b) compression of the supercritical fluid by the high-pressure pump to the desired pressure; c) isothermal initiation of the melting of the substance by controlled reduction in the pressure and simultaneous recording of the changes in the volume and in the heat flux; d) isothermal initiation of the isothermal crystallization of the material by controlled increase in the pressure and simultaneous recording of the changes in the volume and in the heat flux.

18. Method according to claim 9, in which said material in the fluid or liquid state is modified by reducing its temperature below a temperature at the controlled pressure of the supercritical fluid.

19. Method according to claim 9 further comprising using polymer material to determine when the supercritical fluid/polymer solution is in an equilibrium state and when this solution becomes saturated.

20. Method according to claim 19, further comprising inducing the transition of the polymer by varying the temperature at constant pressure.

21. Method according to claim 20, further comprising, under the same pressure conditions, obtaining a homogeneous, saturated supercritical gas/polymer system using slow heating, followed by condensing a microfoam or nanofoam phase using slow cooling, and recording all the parameters (P, T, $\Delta H$ and $\Delta V$) of the observed transitions during the heating and cooling.

22. Method according to claim 19, further comprising inducing the transition of the polymer by varying the pressure at constant temperature.

23. Method according to claim 22, in which, further comprising, under the same pressure conditions, obtaining a homogeneous, saturated supercritical gas/polymer system using slow heating, followed by a condensing a microfoam or nanofoam phase by slow compression, and recording all the parameters (P, T, $\Delta H$ and $\Delta V$) of the observed transitions.

24. Method according to claim 1, further comprising utilizing the stable shape of the thermogram, which does not change during the successive transitions under the atmosphere of the supercritical gas, as an indicator of the end of formation of the new microfoam or nanofoam phase.

25. The apparatus of claim 1, wherein the apparatus is adapted to measure the variation of pressure of the supercritical fluid, temperature of the cell and volume of the specimen in the cell in situ.

26. The method of claim 9, wherein the variation of pressure of the supercritical fluid, temperature of the cell and volume of the specimen in the cell are measured in situ.

* * * * *